Sept. 10, 1974 A. W. FISCHER Plant Pat. 3,612
AFRICAN VIOLET
Filed May 3, 1973
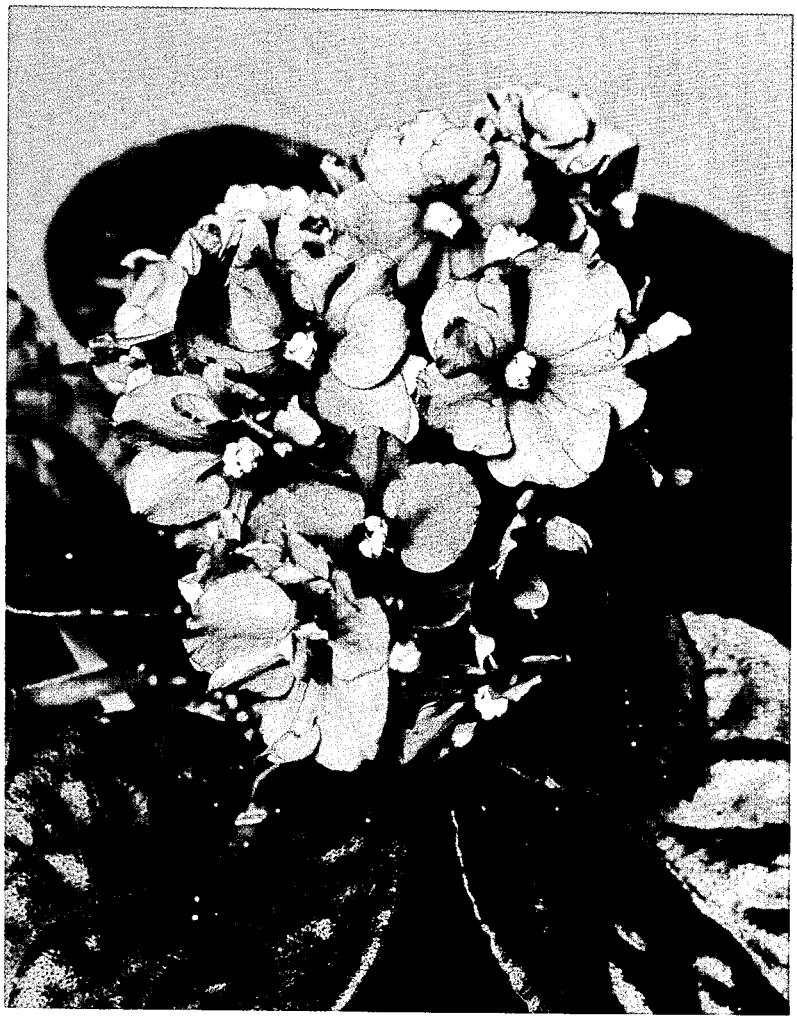

United States Patent Office

Plant Pat. 3,612
Patented Sept. 10, 1974

3,612
AFRICAN VIOLET

Arnold W. Fischer, Isernhagen, Germany, assignor to Geo. J. Ball, Inc., West Chicago, Ill.

Filed May 3, 1973, Ser. No. 357,075
Int. Cl. A01h 5/00
U.S. Cl. Plt.—69 1 Claim

ABSTRACT OF THE DISCLOSURE

A new variety of African violet plant having a very light blue flower coloring, the new plant being of the compact potted plant type in which the flowers are borne upright, converging toward the center to form a dense canopy of long lasting blooms which are borne in clusters on each peduncle.

BACKGROUND OF THE NEW PLANT

This new variety of African violet plant originated as a seedling, in my greenhouse at Isernhagen, Hanover, Germany, from a cross made by me of two varieties selected from my stock of breeding plants maintained by me and crossbred with the objective of producing improved and significantly different plants for the commercial market. The present plant was selected by me for propogation and testing purposes because of the unusual pale blue color of its blossoms and its tendency to produce a rather dense crown appearing above a horizontal spread of abundant and large leaves. Asexual propagation of this new African violet plant, carried on by me at Isernhagen, Hanover, Germany, by means of leaf cuttings, has demonstrated that its distinctive characteristics are firmly fixed and hold true from generation to generation; and commercial propagation of this plant by leaf cuttings and division of shoots is now being done at West Chicago, Illinois, as well as at Isernhagen, Germany.

DESCRIPTION OF THE DRAWING

My new variety of African violet plant is illustrated by the accompanying full color photographic drawing which shows the form and color characteristics of the blooming plant, the color reproductions being as nearly true as is reasonably possible to obtain by means of conventional professional photographic procedures.

DESCRIPTION OF THE NEW PLANT

The following is a detailed description of my new African violet plant with color designations according to the Horticultural Colour Chart (HCC) produced by Robert F. Wilson for The British Colour Council and published in collaboration with The Royal Horticultural Society at London, England.

THE PLANT

Origin: Seedling.
Parentage:
Seed Parent—#66-1.
Pollen Parent—#069-1.
Both parents being plants so identified in my records and maintained in my stock of plants maintained for breeding purposes.

Classification:
*Botanic.*—*Saintpaulia ionantha.*
*Commercial.*—Potted plant type of African violet.
Form: Compact potted plant.
Height: About 4 inches from soil level to top of flowers.
Growth: Condensed and vigorous, with fairly strong leaf petioles which tend to spread horizontally in rotary fashion.
Foliage: Abundant in quantity.

*Size of Leaf.*—About 2¾ inches wide x 3 inches long.
*Shape of Leaf.*—Nearly orbicular.
*Texture.*—Tomentose.
*Ribs and Veins.*—Pinnate and prominent on the under side of leaf, usually with four very obvious veins on each side of the central stem.
*Color.*—*Upper Side*—Ivy Green 1060/2.
*Under Side.*—Veronese Green 660/3.
*Petioles.*—Length varies with age, averaging about 3 inches long in the adult leaf.

THE BUD

Form: Ball shaped.
Size: Small. ¼ inch in diameter and ¼ inch in depth at time of opening.
Opening Rate: Very slow, about five weeks from visible bud to opening of flower.
Color: When petals begin to unfurl:
*Top Petals.*—Campanula Violet 37/1.
*Lower Petals.*—Sea Lavender Violet 637/2.
Sepals: Enclose bud for a very short time. Then sepals open, spear shaped and upstanding.
*Color.*—*Inside.*—Fern Green 0862. *Outside.*—Maroon 1030.
Calyx: Funnel-shaped and synsepalous. Splits to star-shaped.
*Aspect.*—Smooth on inside, hairy on outside.
Peduncle:
*Length.*—½ to ¾ inch from stalk to base of bud.
*Aspect.*—Hairy on outside.
*Strength.*—Sturdy, erect and slender.
*Color.*—Maroon 1030.

THE FLOWER

Blooming Habit: Profuse and recurrent the year around.
Borne: In clusters on each stem or stalk. The inflorescence is a cyme.
Size of Flower: Large.—Diameter.—1½ inches and often more.
Shape of Flower: Cup-shaped when bloom first opens, flattening out as bloom matures.
Petalage: Five petals, basically, plus many petaloids in the upper section and a few in the lower section. Petaloids vary.
*Arrangement.*—Sympetalous.
*Form.*—Rotate with bilateral symmetry and wavy margins.
*Color.*—*Top Side.*—Hyacinth Blue 40/1 in general representation. Reverse Side.—Lobelia Blue 41/2 to 41/3.
*Texture.*—Soft.
Peduncle; Main Stem: 1¼ to 2 inches from base to flower branching.
*Strength.*—Sturdy and upright.
*Color.*—Maroon 1030.
Discoloration After Full Bloom: Color darkens to Moorish Blue 739/2 as a general representation.
Effect of Weather: Hot weathar suppresses flowering and fades the color. Plant thrives in 80% to 90% humidity.
Persistence: Petals hang on and dry.
Disease Resistance: This plant has a natural resistance to known common diseases.
Fragrance: None.
Lasting Quality: 10 to 14 days for the fully opened flower.

REPRODUCTIVE ORGANS

Stamens:
*Anthers.*—Two in number, occasionally 3 or 4 on semi-double blooms, each ⅛ inch long and made up of two anthers fused together.
*Filaments.*—3/16 to ¼ inch long. Color: Hyacinth Blue 40.

*Pollen.*—Color—White.
Pistils: One. Style—⅜ inch long.
Stigmas.—Color—Hyacinth Blue 40.
Ovary: Tomentose. Color—Sap Green 62/3.

This variety of African violet is particularly distinguished by its light blue flower color, each flower exhibiting several petaloids in its upper half and the lower half showing two petaloids in addition to the usual petals, thus presenting a "full" flower which is sometimes semi-double. As a whole, the plant has an attractive form, all flowers being borne upright and converging toward the center of the plant to form a dense canopy of long lasting blooms above lustrous radially spreading foliage.

I claim:

1. A new variety of African violet plant, substantially as herein shown and described, characterized by its profuse production of large pale blue flowers on upright stems which converge to the center of the plant above an abundant spread of horizontally extending foliage.

No references cited.

ROBERT E. BAGWILL, Primary Examiner